United States Patent
Yamamoto et al.

(10) Patent No.: US 8,506,484 B2
(45) Date of Patent: Aug. 13, 2013

(54) ULTRASONIC IMAGING DEVICE

(75) Inventors: Mariko Yamamoto, Kukubunji (JP);
Kunio Hashiba, Tokyo (JP); Takashi Azuma, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 750 days.

(21) Appl. No.: 12/523,088

(22) PCT Filed: Jan. 16, 2008

(86) PCT No.: PCT/JP2008/050392
§ 371 (c)(1),
(2), (4) Date: Jul. 14, 2009

(87) PCT Pub. No.: WO2008/087955
PCT Pub. Date: Jul. 24, 2008

(65) Prior Publication Data
US 2010/0049053 A1 Feb. 25, 2010

(30) Foreign Application Priority Data
Jan. 16, 2007 (JP) ................................. 2007-006635

(51) Int. Cl.
*A61B 8/00* (2006.01)
(52) U.S. Cl.
USPC .......... 600/437; 600/407; 600/443; 600/447; 600/459; 73/625; 73/626; 310/334
(58) Field of Classification Search
USPC .......... 600/437, 443, 447, 459; 73/625–626; 310/334
See application file for complete search history.

(56) References Cited

U.S. PATENT DOCUMENTS

| 6,736,779 B1 * | 5/2004 | Sano et al. .................. 600/447 |
| 2004/0174773 A1 | 9/2004 | Thomenius et al. |
| 2004/0267126 A1 | 12/2004 | Takeuchi |
| 2005/0075570 A1 | 4/2005 | Shinomura et al. |
| 2005/0124880 A1 | 6/2005 | Shinomura et al. |

FOREIGN PATENT DOCUMENTS

| EP | 1 484 019 A1 | 12/2004 |
| EP | 1 247 490 B1 | 7/2008 |
| JP | 2001-190551 | 7/2001 |
| JP | 2001-286467 | 10/2001 |
| JP | 2003-260055 | 9/2003 |
| JP | 2004-274756 | 9/2004 |
| JP | 2005-034633 | 2/2005 |
| WO | WO 01/50961 A1 | 7/2001 |
| WO | WO 03/075768 A1 | 9/2003 |
| WO | WO 2006/134686 A1 | 12/2006 |

* cited by examiner

*Primary Examiner* — Unsu Jung
*Assistant Examiner* — Joseph M Santos
(74) *Attorney, Agent, or Firm* — Antonelli, Terry, Stout & Kraus, LLP.

(57) ABSTRACT

An ultrasonic imaging device which narrows the width of annular areas to be established, without increasing the number of channels. The controller establishes the annular areas 421 to 42p the number of which is larger than the number of signal lines, along line intersections between wave surfaces 51 to 54 of reflective waves and a multi-dimensional surface of the probe 1. The controller selects multiple annular areas (0, 0), (0, 1), and (0, 2) with focal depths differing, for example, by an integral multiple of the ultrasonic wavelength λ, out of the multiple annular areas being established, and connects the multiple transducer elements positioned within the selected multiple annular areas with an identical signal line. Accordingly, the received signals from the selected multiple annular areas arrive at multiple time points shifted by the time corresponding to the wavelength, and the signals do not cancel one another out.

9 Claims, 16 Drawing Sheets

ULTRASONIC IMAGING DEVICE

CROSS REFERENCE TO RELATED APPLICATION

This application is a National Stage Entry of PCT/JP2008/050392 filed Jan. 16, 2008, and claims priority from Japanese Patent Application No. 2007-006635, filed on Jan. 16, 2007, the contents of which are incorporated herein by reference in their entirety.

TECHNICAL FIELD

The present invention relates to an ultrasonic imaging device, and more particularly, it relates to a medical ultrasonic imaging device having a probe including a two-dimensional (2D) matrix array of transducer elements and having a configuration in which multiple output signals of transducer elements are bundled together to each channel so that the number of channels is less than that of transducer elements.

BACKGROUND ART

In recent years, an ultrasonic imaging device endowed with a three-dimensional imaging function is rapidly shifting to a phase of commercialization and clinical application. Such an ultrasonic imaging device endowed with the three-dimensional imaging function employs a probe which incorporates a large number of transducer elements, for example, around a few thousands of elements. Therefore, it is necessary to bundle output signals in units of multiple transducer elements, and to reduce the number of signals, down to the number from 100 to 200, which corresponds to the number of I/O channels of the imaging device main unit.

Patent document 1 discloses a configuration that a phasing circuit is divided into two stages; storing in a probe, a sub-focusing circuit in which multiple transducer elements are bound into one sub-channel, and storing in the device main unit, a main-focusing circuit in which multiple sub-channels are bound into one channel. With the configuration, the sub-channel shape and the channel shape are dynamically controlled, and a width of the transducer elements, which are bound into the same channel, is made to be the same as the distribution width of one transducer element, irrespective of a deflective direction, whereby deterioration of beams can be suppressed.

Patent document 2 discloses a configuration that the two-dimensional array transducer elements 20 are divided into multiple concentric ring areas about a perpendicular line dropped from a wave transmission or wave receiving focal point, and a group of transducer elements within a concentric ring area are connected to one signal line (see FIG. 2 of the patent document 2). The group of transducer elements within the ring area has an approximately the same distance from the focal point, and receiving signals of each transducer element are approximately in phase. Signals in phase do not cancel one another out even though they are added together. Therefore, according to the configuration as disclosed in the patent document 2, a group of transducer elements in the ring area is connected to one signal line, and the signals in the group of transducer elements are bound together. Thereafter, an identical delay amount is given to the bound signals, and they are added to signals of a signal line to which a group of transducer elements in other ring area is connected, whereby phasing is performed. Accordingly, the number of signal lines (the number of channels) can be reduced to the number of the ring areas, and since it is sufficient for a delay circuit to be installed for each of the signal lines, the number of the delay circuits can be reduced as well.

[Patent document 1]
Japanese unexamined patent application publication No. 2005-34633
[Patent document 2]
Japanese unexamined patent application publication

DISCLOSURE OF THE INVENTION

Problem to be Solved by the Invention

However, according to the two-stage phasing circuit as disclosed in the patent document 1, the number of channels is not sufficiently reduced at the time of outputting from the sub-focusing circuit, and there still exist around a few hundreds of channels between the sub-focusing circuit and the main-focusing circuit. In implementation, a portion between the sub-focusing circuit and the main-focusing circuit corresponds to a cable which connects the probe and the device main unit. In order to prevent a loss of operability of the device with the cable which binds a few hundreds of channels, it is necessary to develop a dedicated cable which is much smaller in diameter than a general-purpose cable. However, since it costs high to develop such dedicated cable, there is a problem that it may bring up the price of the device.

In the technique to divide the ring area as disclosed in the patent document 2, if a width of one ring area (a difference between a diameter of inner periphery and a diameter of outer periphery) is large, a phase difference in signals becomes not ignorable, between the transducer elements in proximity to the inner periphery and the transducer elements in proximity to the outer periphery. Then, when a group of the transducer elements is bound together into one signal line, the signals may cancel one another out, thereby reducing the precision in phasing. Since the number of the settable ring areas is the same as the number of signal lines, the ring area cannot be narrowed to a width equal to or less than a predetermined value.

An object of the present invention is to provide an ultrasonic imaging device which establishes annular areas each having a narrowed width, without increasing the number of channels, thereby enabling enhancement of a focused sound pressure.

Means to Solve the Problem

In order to achieve the above object, the ultrasonic imaging device according to a first aspect of the present embodiment includes multiple transducer elements arranged in two-dimensional surface, a probe having the multiple transducer elements for transmitting an ultrasonic wave to a predetermined focal point and receiving a reflected wave therefrom, multiple signal lines the number of which is less than the number of the transducer elements, a selection part for connecting the multiple transducer elements with any of the signal line being selected out of the multiple signal lines, a controller for controlling an operation of the selection part, and a beamformer for delaying signals outputted from the multiple signal lines by a predetermined amount with respect to each of the signal lines, and summing the signals, wherein, the controller establishes annular areas the number of which is larger than the number of signal lines, along with line intersections between wave surfaces of the reflected wave and the two-dimensional surface. The controller selects out of the multiple annular areas being established, multiple annular areas with focal depths differing by an integral multiple of an ultrasonic wavelength, and controls the selection part to connect the transducer elements positioned within the selected multiple annular areas with an identical signal line.

With the configuration above, it is possible to establish the annular areas the number of which is larger than the number of signal lines, thereby narrowing the width of the annular area. Accordingly, since the signals of the transducer elements within the same annular area are distributed within a narrow duration, the phase shift amount becomes small, and thereby reducing the possibility that signals cancel one another out, when addition is performed by the connection with the same signal line. Furthermore, multiple annular areas are selected, whose focal depths differ by an integral multiple of the ultrasonic wavelength, and the signals received from the selected multiple annular areas arrive at multiple time points being shifted by the time length corresponding to the wavelength, and these signals do not cancel one another out. Accordingly, it is possible to prevent the signals from cancelling one another out, without increasing the number of signal lines (the number of channels), thereby improving the focused sound pressure.

It is possible to configure such that the controller assumes multiple concentric spheres, each being different by a predetermined value in radius centering the focal point, and establishes areas sectioned by the line intersections between the multiple concentric spheres and the two-dimensional surface, as the annular areas. By way of example, if it is assumed that the number of signal lines is M, a predetermined integer between or equal to 1 and M is $N_1$, and the ultrasonic wavelength is $\lambda$, the radius of the multiple concentric spheres varies by $\lambda/N_1$, so as to establish the annular areas. Accordingly, the delay amounts of the multiple signal lines become values varying by a certain quantity, enabling an accurate delaying.

It is preferable for the controller to select the annular areas not adjacent to each other. It is further possible to configure such that the controller establishes a nonuse annular area between adjacent annular areas, and the selection part does not connect the transducer elements positioned in the nonuse annular area with any signal lines.

If a focal position is changed, it is preferable that the controller modifies the position of the annular areas and the selection thereof. Therefore, the controller is capable of performing an arithmetical operation in advance to establish and select the annular areas, with respect to each position that can be set as the focal point, and storing a result of the operation in a storage. Upon receipt of the reflected wave, the controller reads the operation result stored in the storage, according to the focal position at that point of time, and controls the selection part. With this configuration, it is not necessary to perform the arithmetical operation every time when the focal position is changed, and therefore, it is possible to respond quickly to the change of the focal position.

In order to achieve the object as described above, the ultrasonic imaging device according to a second aspect of the present invention is provided with multiple transducer elements which are arranged in two-dimensional array in the first direction and in the second direction, a probe having the multiple transducer elements for transmitting an ultrasonic wave of wavelength $\lambda$ to a predetermined focal point and receiving a reflected wave, M signal lines the number of which is less than the number of the transducer elements, a selection part for connecting the multiple transducer elements with any of signal line selected out of the multiple signal lines, a controller for controlling an operation of the selection part, and a beamformer for delaying the signals outputted from the multiple signal lines by a predetermined amount with respect to each of the signal lines, and summing the signals, wherein when it is assumed that a maximum value of a distance between the focal point and the multiple transducer elements is $R_{max}$, a minimum value of the distance between the focal point and the multiple transducer elements is $R_{min}$, a distance between the focal point and the transducer elements at i-th position and j-th position respectively in the first direction and the second direction is $R_{ij}$, a predetermined actual number between or equal to $R_{min}$ and $R_{max}$ is $R_0$, a predetermined integer between or equal to 1 and M is $N_1$, an arbitrary integer between or equal to 0 and $N_1-1$ is $n_1$ ($n_1=0, 1, \ldots N_1-1$), a predetermined integer between or equal to 0 and $(R_{max}-R_0)/\lambda$ is $N_2$, and an arbitrary integer between or equal to 0 and $N_2-1$ is $n_2$ ($n_2=0, 1, \ldots N_2-1$), the controller establishes the annular area for each combination of $n_1$ and $n_2$, the annular area being made up of multiple transducer elements having $R_{ij}$ which satisfies the formula 1 as the following:

$$R_0+n_2 \cdot \lambda+n_1 \cdot (\lambda/N_1) < R_{ij} \leq R_0+n_2 \cdot \lambda+(n_1+1) \cdot (\lambda/N_1) \qquad \text{(formula 1)}$$

The controller selects predetermined multiple annular areas out of the multiple annular areas being established, and controls the selection part to connect the transducer elements constituting the multiple annular areas being selected with an identical signal line.

Accordingly, it is possible to set $N_1 \times N_2$ annular areas the number of which is larger than the number of the signal lines, thereby narrowing the width of the annular areas. Therefore, even when the signals of the transducer elements within the same annular area are added, it is possible to reduce the occurrence that the signals cancel one another out. Since each of the multiple annular areas varies by $\lambda/N_1$ in the distance from the focal point, the delay amounts of the multiple signal lines become values varying by a certain quantity, enabling an accurate delaying. Accordingly, it is possible to prevent that the signals cancel one another out, without increasing the number of signal lines (the number of channels), thereby improving the focused sound pressure.

It is possible to configure such that the controller selects multiple annular areas with focal depths differing by an integral multiple of an ultrasonic wavelength. By way of example, when the annular areas established by the combination of $n_1$ and $n_2$ are represented as $(n_1, n_2)$ in the formula 1, the controller selects $N_2$ annular areas represented by $(m, 0)$, $(m, 1)$, $(m, 2) \ldots (m, N_2-1)$ for the m-th signal line, and connects the transducer elements in these annular areas with the signal line. Accordingly, receiving signals in the selected multiple annular areas are shifted in arrival time corresponding to the distance $\lambda$, and the signals do not cancel one another out. Therefore, it is possible to enhance the focused sound pressure.

Effect of the Invention

In the ultrasonic imaging device according to the present invention, annular areas which are narrow in width can be established, the number of which is larger than the number of the signal lines, and therefore, it is possible to obtain received pulses which are distributed within a narrow duration. In addition, when multiple annular areas are selected to be connected with one signal line, the annular areas targeted for selection have distances from the focal point being different by the ultrasonic wavelength, and the arrival time points of the pulses respectively in these annular areas are shifted by the time length corresponding to the ultrasonic wavelength on the time axis, thereby preventing the occurrence that pulses cancel one another out. Accordingly, even when a deflection angle is large, the focused sound pressure can be amplified without bringing about canceling of sound pressure in a delay addition process, and in any place other than the front side of the probe, it is possible to obtain an image having a quality nearly the same as that of the front face of the probe.

As discussed above, the present invention does not need to increase the number of signal lines, and therefore, a general-purpose cable can be implemented between the probe and the device main unit. In addition, the focused sound pressure can be improved by around 100% to 300%. Even when the deflection angle is large, a sufficient focused sound pressure can be ensured, and therefore it is possible to implement an ultrasonic imaging device with a low cost, which is capable of obtaining an image having a quality nearly the same as the image quality in front of the probe, even in the place other than the front side of the probe.

In addition, the width of the annular area can be narrowed to the width of the transducer element to the extreme. In the case above, if a delay time is given to the signal line, adjacent transducer elements can be provided with delay times different respectively, thereby enabling a highly qualified three-dimensional imaging.

BEST MODE FOR CARRYING OUT THE INVENTION

Hereinafter, preferred embodiments of the present invention will be explained in detail with reference to the accompanying drawings.

First Embodiment

Firstly, a configuration of the ultrasonic imaging device according to the first embodiment will be explained with reference to FIG. 1, FIG. 2, and FIG. 3. As shown in FIG. 1, the ultrasonic imaging device according to the present embodiment includes a probe 1, an device main unit 3, and a selection part 2 connecting the elements above.

As shown in FIG. 2, the probe 1 includes N transducer elements $1a1$ to $1aN$, which are set in array, two-dimensionally in the first direction 11 and in the second direction 12, to transmit and receive ultrasonic waves having a predetermined wavelength. The selection part 2 establishes multiple annular areas, depending on the focal positions, on a two-dimensional surface where the transducer elements of the probe 1 are arranged, and performs switching to select predetermined annular areas out of the multiple annular areas, to connect the transducer elements included in these selected annular areas with one signal line. Other predetermined multiple annular areas are connected to another signal line. The procedure above is conducted for all the annular areas, thereby establishing coupling with the device main unit 3 via the signal lines, the number of which is less than the number of the annular areas.

Specifically, the probe 1 and the selection part 2 are configured as shown in FIG. 3. The selection part 2 includes N switches $2a1$ to $2aN$, and M signal lines $2b1$ to $2bM$. N switches $2a1$ to $2aN$ are connected to N transducer elements $1a1$ to $1aN$ of the probe 1, at a ratio of 1:1, via N signal lines. Each of the switches $2a1$ to $2aN$ selectively connects N transducer elements $1a1$ to $1aN$ with any of M signal lines $2b1$ to $2bM$ in response to a directive from the controller 11 of the device main unit 3. On this occasion, as described below, the controller 11 virtually divides the two-dimensional surface, on which the transducer elements are arranged, into multiple annular areas, selects a predetermined number of annular areas out of the multiple annular areas, and outputs control signals to each of the switches $2a1$ to $2aN$, so that a group of the transducer elements included in the selected annular areas is connected to one signal line.

Accordingly, since multiple transducer elements positioned in the predetermined number of annular areas are connected to an identical one signal line, at the time of wave receiving, multiple signals outputted from these multiple transducer elements are made to flow through one signal line, whereby the signals are added together to be bound into one signal. Therefore, at the time of wave receiving, N signals from N transducer elements $1a1$ to $1aN$ can be reduced to M, and outputted to the device main unit 3.

As shown in FIG. 1, the device main unit 3 incorporates a transmit-receive separation switch 4, a transmit beam former 5, an amplifier 6, a receive beam former 7, a signal processor 8, a three-dimensional memory 9, a display part 10, and the controller 11. The transmit-receive separation switch 4 is connected to the selection part 2, so as to couple the transmit beam former 5 with the selection part 2 at the time of transmission, and couple the amplifier 6 with the selection part 2 at the time of receiving.

At the time of wave receiving, each of the received signals bound into M by the selection part 2 are amplified by the amplifier 6, and the signals are subjected to the delay process in the receive beam former 7 for delaying the signals by a predetermined delay time with respect to each of the M signal lines. Thereafter, an addition process is performed for binding the signals of M signal lines into one, thereby subjecting the signals to phasing addition, and further converted into digital signals to make received data. Therefore, the receive beam former 7 is provided with delay circuits respectively for M signal lines.

The received data outputted from the receive beam former 7 is subjected to a signal processing to constitute an image in the signal processor 8, and the result is accumulated in the three-dimensional memory 9. Then, the image is displayed on the display part 10.

At the time of wave transmission, in response to a directive from the controller 11, the transmit beam former 5 rotates the phase of the signals of predetermined frequency by a certain amount and passes the delayed signals to the transmit-receive separation switch 4, in order to transmit a certain ultrasonic wave to the transducer elements $1a1$ to $1aN$ at the predetermined focal position. The transmit-receive separation switch 4 passes the signals to each of the transducer elements $1a1$ to $1aN$ via the selection part 2. The selection part 2 is able to perform switching at the time of wave transmission as well, in the similar manner as the wave receiving time. Alternatively, as far as the wave transmission is possible to the predetermined focal position, other method may be employed to perform switching.

After carrying out an operation for setting the annular areas, the controller 11 establishes the annular areas as a result of the operation, and controls the selection part 2 to connect the transducer elements positioned in the selected annular areas, with a predetermined signal line. In addition, the controller 11 controls each part of the device main unit 3, so that a transmission beam direction, a receive beam direction, a delay time, displaying, and the like are controlled.

FIG. 4 illustrates a detailed configuration of the controller 11. The controller 11 incorporates an I/O part 111, a CPU 112, ROM 113, and RAM 114. The RAM 114 stores a pattern calculation program 1141 and a setting file 1142. The pattern calculation program 1141 establishes annular areas by performing an arithmetical operation depending on a focal position, further selects annular areas, and calculates correspondences (channel number reducing pattern) which indicate how the transducer elements within the selected annular areas are connected to a predetermined signal line. The CPU 112 reads and executes the pattern calculation program 1141 when initial settings such as factory default settings are configured in the ultrasonic imaging device, then the CPU calculates the channel number reducing patterns respectively for the settable focal positions and after-mentioned parameters ($R_0$, $N_1$, $N_2$, $n_3$) settable by the user, and stores the result of the calculation in the setting file 1142 in the RAM 114. When an ultrasonic imaging is actually performed, the CPU 112 reads from the setting file 1142, the channel number reducing pattern which is associated with the focal position and the parameters ($R_0$, $N_1$, $N_2$ and $N_3$) set by the user at that point of time, and passes the channel number reducing pattern to the selection part 2. The selection part 2 operates the switches 2a1 to 2aN of the selection part 2, according to the channel number reducing pattern being received, and couples predetermined transducer elements with a predetermined signal line.

Here, with reference to FIG. 5 and FIG. 6(a) and FIG. 6(b), an explanation will be made regarding an overview of the operation performed by the controller 11 to achieve the channel number reduction at a ratio of N to M.

FIG. 5 illustrates a basic pattern of annular areas established on the probe 1 by the controller 11. A point sound source 411 is assumed as the focal point 410. On the transducer elements 1a1 to 1aN of the probe 1, annular areas 421 to 42p are set, being in the shapes along line intersections 420, between wave surfaces (sphere surfaces) 412 of the ultrasonic waves (reflected waves) generated by the point sound source 411, and a two-dimensional array surface 110 of the probe 1.

In other words, when it is assumed that the wavelength of the ultrasonic wave received by the probe 1 is $\lambda$, a maximum value of the distance between the focal point 410 and the multiple transducer elements 1a1 to 1aN is $R_{max}$ 43, a minimum value of the distance between the focal point 410 and the multiple transducer elements 1a1 to 1aN is $R_{min}$ 44, a distance between each of the transducer elements and the focal point is $R_{ij}$, each transducer element being placed at the i-th position and the j-th position respectively in the first direction 11 and the second direction 12 of the probe 1, a distance between one end of the area on the probe 1 where the annular areas are to be established according to the formula 1 and the focal point is $R_0$ 45 (an actual number between or equal to $R_{min}$ and $R_{max}$), the number of output signals from the selection part is M, a predetermined integer between or equal to 1 and M is $N_1$, an arbitrary integer between or equal to 0 and $N_1-1$ is $n_1$ ($n_1=0, 1, \ldots N_1-1$), a predetermined integer between or equal to 0 and $(R_{max}-R_0)/\lambda$ for defining the other end of the area to which the annular areas are to be established according to the following formula 1 is $N_2$, and an arbitrary integer between or equal to 0 and $N_2-1$ is $n_2$ ($n_2=0, 1, \ldots N_2-1$), the annular areas 422 to 42p are made up of a group of transducer elements of $R_{ij}$ satisfying the following formula 1, with respect to each of the combinations $n_1$ ($n_1=0, 1, \ldots N_1-1$) and $n_2$ ($n_2=0, 1 \ldots N_2-1$). It is to be noted that $N_1$ indicates the number of signal lines ($1 \leq N_1 \leq M$) to be connected with the transducer elements of the annular areas established by the formula 1, indicating a priority setting for a resolving power in the sound axis direction and a focused sound pressure.

$$R_0+n_2\cdot\lambda+n_1\cdot(\lambda/N_1) < R_{ij} \leq R_0+n_2\cdot\lambda+(n_1+1)\cdot(\lambda/N_1) \quad \text{(formula 1)}$$

With reference to FIG. 6(a) and FIG. 6(b), annular areas established by the formula 1 will be explained. In the formula 1, the term of ($R_0+n_2\cdot\lambda$) is included in each of the left hand side and the right hand side. According to this term, as shown in FIG. 6(a), $N_2$ wave surfaces 51 to 54 at distances from the focal point being ($R_0+n_2\cdot\lambda$) ($n_2=0, 1, \ldots N_2-1$), and the annular areas 51a to 54a sectioned by the line intersections between $N_2$ wave surfaces 51 to 54 and the two-dimensional surface of the probe 1 are sequentially configured outwardly from $R_0$ being one end on the two-dimensional surface of the probe 1. Spacing between the wave surfaces 51 to 54 corresponds to the ultrasonic wavelength $\lambda$.

In addition, in the formula 1, the terms of $n_1\cdot(\lambda/N_1)$ and $(n_1+1)\cdot(\lambda/N_1)$ are included respectively in the left hand side and the right hand side. With these terms, each the values ($n_1=0, 1, \ldots N_1-1$) is set to $n_1$, for each of the values of $n_2$ ($n_2=0, 1, \ldots N_2-1$), and accordingly, as shown in FIG. 6(b), each of the annular areas 51a to 54a established in FIG. 6(a) are further divided into $N_1$ areas by the wave surfaces at distances from the focal point being different by $\lambda/N_1$. Therefore, the annular areas 422 to 42p are set, which are sectioned by the line intersections between the wave surfaces at the distances from the focal point, being different by $\lambda/N_1$, and the two-dimensional surface of the probe 1. The number of annular areas 422 to 42p being established by the formula 1 is based on the combination of $n_1$ and $n_2$, and therefore it is $N_1 \times N_2$. When the annular areas defined by the formula 1 according to the combination of $n_1$ and $n_2$ are represented by ($n_1, n_2$), if $N_1=4$ and $N_2=3$ as shown in FIG. 6(b), four areas (0, 0), (1, 0), (2, 0), and (3, 0) are set in the area 51a when $n_2=0$. When $n_2=1$, four areas (0, 1), (1, 1), (2, 1), and (3, 1) are set in the area 52a, and when $n_2=2$, four areas four areas (0, 2), (1, 2), (2, 2), and (3, 2) are set in the area 53a.

The transducer elements positioned inner and/or outer than the annular areas 422 to 42p established by the formula 1 are associated with arbitrary number $n_3$ of the annular areas 421 and the like, being reserved separately. In the case of FIG. 6(a), the area 421 corresponds to an area between the line intersection of the wave surface $R_0$ and the probe 1, and the end of the probe 1 on the $R_{min}$ side. This area 421 is connected in any of (M−$N_1$) signal lines being reserved.

With reference to FIG. 7, a method for establishing the annular areas 421 to 42p will be explained, by taking a specific example, when $N_1=4$ and $N_2=2$. As shown in FIG. 7, the two-dimensional surface of the probe 1 is sectioned into $N_2=2$ areas 461 and 462, by the line intersections 471, 472, and 473 between the two-dimensional surface and the wave surfaces from $R_0$ 45=481, with the spacing of $\lambda$. Borders (line intersections) 471, 472, and 473 of each of the areas are positioned at the distances from the focal point 410 by the lengths 481, 482, and 483 which are respectively represented by $R_0$, $R_0+\lambda$, $R_0+2\cdot\lambda$. Next, the inside of each of the areas 461 and 462 is divided into $N_1=4$ annular areas 491, 492, 493, and 494, by the line intersections 4102 to 4104 between the wave surfaces with the spacing of $\lambda/N_1=\lambda/4$ and the two-dimensional surface of the probe 1. Borders (intersection lines) of each area, 4101, 4102, 4103, 4104, 4105, are positioned at the distances from the focal point 410 by the lengths 4111, 4112, 4113, 4114, and 4115 which are respectively represented by $R_0+1\cdot\lambda+0\cdot(\lambda/4)$, $R_0+1\cdot\lambda+1\cdot(\lambda/4)$, $R_0+1\cdot\lambda+2\cdot(\lambda/4)$, $R_0+1\cdot\lambda+3\cdot(\lambda/4)$, $R_0+1\cdot\lambda+4\cdot(\lambda/4)$.

Next, an explanation will be made regarding the annular areas and a selection of signal line which is connected to these annular areas. The selection part 2 selects multiple annular areas not adjacent to each other, out of $N_1 \times N_2$ annular areas being established according to the formula 2, and connects the selected annular areas with one signal line, thereby reducing the number of channels. In other words, when integers between or equal to 0 and $N_1-1$, which represent the numerical numbers of $N_1$ signal lines, are assumed as m (m=0, 1, \ldots $N_1-1$) and the annular areas are represented by ($n_1, n_2$), annular areas having $n_1$ being equal to m ($n_1=m$) and $n_2$ being each value of $n_2=0, 1, \ldots N_2-1$, are all selected as the annular areas (m, $n_2$) ($N_2$ pieces) for the m-th signal line. Then, the transducer elements in those areas are connected to the m-th signal line. Accordingly, the annular areas connected to the signal line m are represented by the formula 2. This is the channel number reducing pattern.

$$(m, n_2) n_2 = 0, 1, \ldots N_2 - 1 \quad \text{(formula 2)}$$

By way of example, in the case as shown in FIG. 6(b), the selection part 2 connects the transducer elements in the annular areas (0, 0), (0, 1), and (0, 2) to the m=0th signal line, connects the transducer elements in the annular areas (1, 0), (1, 1), and (1, 2) to the m=1st signal line, and connects the transducer elements in the annular areas (2, 0), (2, 1) and (2, 2) to the m=2nd signal line.

It is to be noted that the annular areas 421 and the like positioned inner and/or outer than the annular areas 422 to 42p established according to the formula 1, are connected to a signal line m' that is different from the aforementioned $N_1$ signal lines. Alternatively, it is further possible to configure such that the annular areas 421 and the like are not connected to any of the signal lines.

Here, with reference to a flow diagram shown in FIG. 8, a procedure will be explained, according to which the CPU 112 of the controller 11 reads and executes the pattern calculation program 1141, so as to calculate the channel number reducing pattern at the time of initial setting for the ultrasonic imaging device.

Firstly, in the annular area establishing step 51, an operation is carried out to establish correspondences between N transducer elements and the annular areas 421 to 42p. By way of example, this operation is carried out by calculating a matrix A which represents the correspondences between N transducer elements and the annular areas. In the annular area selection step 52, an operation is carried out to establish correspondences between $N_2$ annular areas with one signal line. By way of example, this operation is carried out by calculating a matrix B which represents the correspondences between the annular areas and the signal line. Further in step 53, the correspondences between the N transducer elements and the signal lines are calculated by using the results of the steps 51 and 52. By way of example, if the correspondences between the transducer elements and the annular areas are assumed as A, and the correspondences between the annular areas and the signal is assumed as B, a product of A·B represents a channel number reducing pattern, and therefore, this is calculated by the channel number reducing pattern calculation step 53. In the setting file generation step 54, the channel number reducing pattern is written and stored in the setting file 1142. In those steps 51 to 54, the operations are carried out with respect to each settable focal position and each of the parameters ($R_0$, $N_1$, $N_2$, and $n_3$) settable by the user as described below, and the results are stored in the setting file 1142.

When imaging is performed, the CPU 112 reads from the setting file 1142, a channel number reducing pattern which is associated with the parameters set by the user and the focal point position at that time, and passes the selected pattern to the selection part 2. The selection part performs switching operation according to the pattern being received, thereby achieving the reduction of number of the channels.

With reference to FIG. 9, the annular area setting step 51 will be explained specifically. Firstly, an ultrasonic wavelength λ, coordinates of the transducer elements ($x_{ij}$, $y_{ij}$, 0), and the number of output signal lines M are captured from the memory within the controller 11, and the coordinates of the focal point ($x_f$, $y_f$, $z_f$) are set at an arbitrary position within a possible focusing range which is predefined (step 511). A maximum value $R_{max}$ and a minimum value $R_{min}$ of the distance between the focal point and the transducer elements are calculated (step 512). Next, inputting of distance $R_0$ (an actual number between or equal to $R_{min}$ and $R_{max}$) between the focal point and one end of the area on the probe 1, where the annular area is supposed to be established by the formula 1, is set to be an arbitrary value within a range settable by a user (step 513). Furthermore, an integer $N_1$ between or equal to 1 and M, and an integer $N_2$ (an integer between or equal to 0 and ($R_{max}$−$R_0$)/λ) defining the other end of the area on the probe 1, where the annular area is supposed to be established by the formula 1, are set to be arbitrary values within a range settable by the user (step 514). In addition, $N_1$ represents the number of signal lines ($1 \leq N_1 \leq M$) to which the transducer elements of the annular areas established by the formula 1 are connected, and it indicates a priority setting for the resolving power in the sound axis direction and the focusing sound pressure.

Correspondences are established respectively between the combinations ($n_1$, $n_2$) of $n_1$ ($n_1$=0, 1, … $N_1$−1) and $n_2$ ($n_2$=0, 1, … $N_2$−1), and the transducer elements satisfying the formula 1 into which each of the values from steps 511 to 513 are substituted, and thereby setting $N_1 \times N_2$ annular areas ($n_1$, $n_2$) (step 515)

$$R_0 + n_2 \cdot \lambda + n_1 \cdot (\lambda/N_1) < R_{ij} \leq R_0 + n_2 \cdot \lambda + (n_1 + 1) \cdot (\lambda/N_1) \quad \text{(formula 1)}$$

Finally, the annular areas 421 and the like, the number of which is an arbitrary number $n_3$, are reserved for establishing correspondences with the transducer elements ij which are not associated with any of the annular areas ($n_1$, $n_2$) defined by the formula 1, and correspondences are established between these transducer elements ij and $n_3$ annular areas (step 516). As for the correspondences, it is further possible to prepare multiple types thereof allowing the user to make a selection.

Next, with reference to FIG. 10, the annular area selection step 52 in FIG. 8 will be explained specifically. Firstly, an integer m between or equal to 0 and $N_1$−1 representing the number of the signal lines, and integers ($n_1$, $n_2$) specifying the annular areas are received from step 51 (step 521). Then, all the annular areas specified by the following formula are selected, and correspondences are established between the annular areas and the signal lines specified by m (step 522):

$$(m, n_2) n_2 = 0, 1, \ldots N_2 - 1 \quad \text{(formula 2)}$$

The same procedure is executed for each of the values of m (m=0, 1, 2 … $N_1$−1).

The annular areas the number of which is $n_3$ being set in the aforementioned step 516 are different from the annular areas ($n_1$, $n_2$), and therefore, correspondences are established between these annular areas and the signal line m' which is different from $N_1$ signal lines used in step 521 (step 523). Also for this correspondence, it is further possible to prepare multiple types of correspondences, so as to allow the user to make a selection.

Each of the operations in the steps described above is performed for each of the settable focusing position and for each of the parameters ($R_0$, $N_1$, $N_2$, and $n_3$) settable by the user as described below, and a result of the operations is stored in the setting file 1142.

As discussed above, in the present embodiment, the annular areas the number of which is larger than the number of signal lines are established, and $N_2$ annular areas (m, $n_2$) are connected to the m-th signal line. $N_2$ annular areas (m, $n_2$) are positioned respectively at the distances from the focal point 410 being shifted by λ, and therefore, ultrasonic signals arriving from the focal point 410 (point sound source 411) to the transducer elements in these annular areas, are also shifted in time length which corresponds to the distance λ (2 π as a phase). Accordingly, even though an addition is performed by simultaneously connecting the wave receiving signals from $N_2$ annular areas with the signal line, $N_2$ peaks are formed on different positions (on the time axis), and there is no overlapping between waveforms. Therefore, there is no occurrence that the signals coming from different annular areas cancel one another out.

In addition, the width of the annular areas 422 and 42*p* (a difference between the inner diameter and the outer diameter) becomes narrower, compared to the case where the annular areas are established in such a manner that the number of the areas is equal to the number of the signal lines. In other words, each of the annular areas 51*a* and the like, corresponding to λ as a distance from the focal point 410, is divided into $N_1$, and the width is narrowed to the duration corresponding to $\lambda/N_1$ as a distance from the focal point 410. A phase lag amount between the signals arriving the transducer element in the innermost periphery side and arriving the transducer element in the outermost periphery side, within one of the annular areas 422 to 42*p* is just the phase lag amount ($2\pi/N_1$) corresponding to the distance $\lambda/N_1$ from the focal point 410. Therefore, even though the addition is performed by connecting simultaneously the wave receiving signals of multiple transducer elements within one annular area with the signal lines, it is possible to reduce a phenomenon that the signals of the transducer elements within one annular area cancel one another out.

Therefore, a signal waveform outputted from one signal line has $N_2$ peaks with peak positions shifted by the time corresponding to the wavelength λ (approximately 2 π as a phase), and each one of the peak width (discretization pitch) is narrowed to the duration corresponding to the distance $\lambda/N_1$. This kind of signal waveform extends in the time axis direction, but each of the peaks has a narrow width and being steep.

A phase difference between the signals of M signal lines is $2\pi/N_1$ (i.e., corresponding to the distance $\lambda/N_1$) for each. The receive beam former 7 performs addition by delaying by $2\pi/N_1$, the phase of signals from the M signal lines, achieving an accurate phasing, thereby enabling a reduction of occurrence that the signals cancel one another out at the time of addition by the beam former 7. Accordingly, it is possible to obtain from the beam former 7, output signals having $N_2$ peaks each being narrow in peak width and each being steep. The signal processor 8 performs an image reconstruction by using the output signals. Then, the resolving power in the sound axis is lowered because the output signals are made up of $N_2$ peaks which are shifted in clock time, but since each of the peaks is steep, piece by piece, it is possible to improve several-fold the focused sound pressure.

Hereinafter, by using a specific example, an explanation will be made regarding an operation and effect of the present embodiment. Here, in a example with the channel number reducing pattern of the present embodiment and a comparative example, simulations were performed regarding a temporal waveform of the focused sound pressure and a point image function on a hemisphere face. Then, an explanation will be made numerically, as to an improved effect in the focused sound pressure and image quality enhancement, according to the configuration of the present invention.

As a configuration of the probe 1, the size of each transducer elements 1*a*1 to 1*a*N was set to be 0.3 mm square, the number of transducer elements N was 64 in the major direction 12, and 48 in the minor direction 11, and the number of channels (the number of signal lines M) was set to be 12.

The channel number reducing pattern of the present embodiment was based on the annular area established by the formula 1, assuming that $N_1$=12 and $N_2$=3. According to steps 511 to 616 shown in FIG. 9, 36 annular areas were established as shown in FIG. 11(*a*). (It is to be noted that only 32 annular areas are shown in FIG. 11(*a*) for illustrative purpose.) Accordingly, when the annular areas were represented by ($n_1$, $n_2$), as shown in FIG. 11(*a*), 36 annular areas were established; (0, 0) to (11, 0), (0, 1) to (11, 1) and (0, 2) to (11, 2) (though the annular areas of (8, 2), (9, 2), (10, 2), and (11, 2) are not shown in FIG. 11(*a*), these areas are also established). Next, in the steps 521 to 523 as shown in FIG. 10, annular areas were selected, which were to be connected to the signal lines M=12 according to the formula 2. In other words, every three of annular areas having equal $n_1$ were selected, and these selected areas were connected to one signal line. Specifically, (0, 0), (0, 1), and (0, 2) were connected to the 0th signal line, (1, 0), (1, 1), and (1, 2) were connected to the first signal line. In a similar manner, (m, 0), (m, 1), and (m, 2) were connected to the m-th signal line.

In the comparative example, as shown in FIG. 11(*b*), there were configured eleven wave surfaces having the focusing point 411 as a sound source, and twelve annular areas 1101 to 1112 were established, which were sectioned by the intersection lines between the wave surfaces and the two-dimensional surface of the probe 1. Since spacing of the wave surfaces was constant, the widths of the annular areas 1101 to 1112 on the two-dimensional surface of the probe 1 were not uniform. Here, one annular area was brought into correspondence with one channel. In other words, all the transducer elements included in one annular area were connected to one signal line, thereby connecting twelve annular areas 1101 to 1112 to twelve signal lines, respectively.

As is clear from FIG. 11(*a*) and FIG. 11(*b*), the width of the annular areas for a certain number of signals (M=12) were narrower in the present embodiment, than the comparative example. Therefore, in the present embodiment, a time lag amount between the signal arriving at the transducer element at the innermost periphery and the signal arriving at the transducer element at the outermost periphery within one annular area is ($\lambda/(C \cdot N_1)$) (here, C represents acoustic velocity), and it is smaller than that of the comparative example. Even in the case where the addition is performed by connecting simultaneously the wave receiving signals of multiple transducer elements within one annular area, with the signal lines, it is possible to reduce the phenomenon that the signals of the transducer elements within one annular area cancel one another out.

In addition, the annular areas $N_2$=3, being connected with one signal line, are shifted by λ as a distance from the focal point 410, and therefore, output signals arrive with a time lag corresponding to λ/C (C represents acoustic velocity). Therefore, even though the addition is performed by simultaneously connecting the wave receiving signals from $N_2$=3 annular areas with the signal line, the peaks of $N_2$=3 are formed at different positions (on the time axis), and the waveforms do not overlap one another. Therefore, there is no phenomenon that signals from different annular areas cancel one another out, enabling an accurate delay time control.

Actually, a pulse was received from the focal point, and a signal waveform was calculated according to an arithmetic operation. As conditions for generating the pulse, an amplitude for each transducer element was assumed as constant (=1), and a phase difference as to each element was assumed to be equivalent to the phase difference generated by one-point focusing on each of the focal points (50 mm, 0 mm, and 30 mm). An amplitude waveform in the temporal direction was obtained, assuming that a center frequency was 2.5 MHz, a pulse length was 4 waves, and an envelope curve was raised cosine. FIG. 12(a) shows signal waveforms (a histogram showing the number of pulses for each arrival time), which were obtained by subjecting the wave receiving signals of sonic waves from the sound source at the focal position, to the delay-and-sum by the receive beam former 7. As is clear from FIG. 12(a), the received signals obtained according to the present embodiment formed $N_2=3$ peaks at different positions (on the time axis), and the peak interval 8b1 corresponded to $\lambda/C$ as a distance from the focal point, and there was no overlapping in the peak waveforms. Accordingly, there was no occurrence of phenomenon that the signals from different annular areas cancel one another out. A width of each of the peaks (discretization pitch) was narrower, relative to the peak width 8a of the comparative example as shown in FIG. 12(b). Furthermore, the signal waveforms according to the present embodiment as shown in FIG. 12(a) had three peaks, and therefore, the total width 8b2 of the three peaks extended larger than the comparative example. However, the height of the peaks were not reduced to one-third of the peak height of the comparative example as shown in FIG. 12(b), only showing around 20% to 30% of reduction. Accordingly, there was no steep three peaks being obtained. This is because, in the present embodiment, the peak was divided into three without cancelling one another out, a width of one annular area was narrowed to a duration which corresponds to $\lambda/N_1$ as a distance from the focal point 410, and therefore, even if the received wave signals of multiple transducer elements within one annular area were added, the signal cancelling-out phenomenon was reduced. It is to be noted that a width 8b3 of one peak becomes narrower as $N_1$ becomes larger, and when the width of one annular area is narrowed to the width of transducer element, which is a physical limit, the width of one peak is minimized.

FIG. 13(a) and FIG. 13(b) illustrate temporal waveforms of the focused sound pressure of the signals shown in FIG. 12(a) and FIG. 12(b) respectively. The temporal waveform of the focused sound pressure numerically represents values obtained by taking a convolution of the histogram by arrival time (FIG. 12(a) and FIG. 12(b)) and the pulse waveform. As shown in FIG. 13(a), a value of the maximum sound pressure 9b of the focused sound pressure waveform according to the present embodiment was 2656.7, and it was four times larger than 619.1, which was a value of the focused sound pressure 9a of the comparative example as shown in FIG. 13(b). Therefore, an effect of improvement in the focused sound pressure was obtained. It is to be noted that a vertical axis (focused sound pressure value) of the graphs in FIG. 13(a) and FIG. 13(b), indicates a relative value, assuming a maximum value of the pulses issued from one transducer element is 1 (one). The reasons why the focused sound pressure was improved are as the following; in the present embodiment, as shown in FIG. 12(a), three peak waveforms did not cancel one another out in the histogram by arrival time, and further, the cancelling of signals within each peak was reduced as well, thereby amplifying the focused sound pressure effectively. On the other hand, in the comparative example as shown in FIG. 12(b), the histogram by arrival time was distributed in a continuous wide range, and therefore, pulses which continuously arrived canceled one another out. Next, as shown in FIG. 14, the temporal waveform of the focused sound pressure was integrated with respect to each angle on a hemisphere face, and obtained values were subjected to a point spread function. Then, FIG. 15 was illustrated to represent contour lines of the function, so that an effect on an image quality was evaluated. Firstly, with reference to FIG. 14, a display coordinate system of the point spread function shown in FIG. 15 will be explained. Assuming a central axis as z-axis, a two-dimensional probe 1 was placed on the xy plane of the orthogonal coordinate system (x, y, z), and a beam pattern on the surface of a hemisphere Q having a radius assumed as the focal depth F and a center assumed as $x=y=z=0$, was projected on (u, v) coordinate system which was obtained by normalizing the (x, y) coordinate system by the focal depth F. The coordinate of one point R on the hemisphere surface Q was assumed as $(x_j, y_j, z_j)$, and this point R was able to be represented by $(F, \theta_j, \phi_j)$ coordinate system, each indicating that the focal depth was F, a rotation angle from z-axis was $\theta_j$, and a rotation angle from the x-axis was $\phi_j$. On this occasion, conversion of the point R into the (u, v) coordinate system can be represented by $u_j=\sin\theta_j \sin\phi_j$, $v_j=\sin\theta_j \cos\phi_j$.

When the maximum sound pressure of the present embodiment was assumed as a reference value, FIG. 15 (a), which is a contour plot of the point spread function of the present embodiment, shows that the focused sound pressure 11b1 was 0.0 dB, and a maximum grating level 11b2 was −24.5 dB. On the other hand, FIG. 15(b), which is a contour plot of the comparative example, shows that the focused sound pressure 11a1 was −24.0 dB, and the maximum grating level 11a2 was −25.0 dB. Accordingly, it is found that in the present embodiment, relative to the comparative example, a difference between the focused sound pressure and the maximum grating level was improved by approximately 25 dB. Therefore, according to the present embodiment, it is possible to suppress a virtual image by approximately 25 dB. It is further to be noted that in both FIG. 15(a) illustrating the present embodiment and FIG. 15(b) illustrating the comparative example, a difference between the maximum sound pressure and the minimum sound pressure was almost the same 75 dB, and therefore, it is found that there were no difference in noise level between the present embodiment and the comparative example. In FIG. 15(a) of the present embodiment, −3 dB main lobe width was 2.0 degrees, whereas in FIG. 15(b) of the comparative example, it was 2.2 degrees. Therefore, it is found that according to the present embodiment, if the focal depth is approximately 58 mm, the resolving power can be improved by approximately 0.1 mm.

As discussed above, it is found that according to the present embodiment, an effect of image quality improvement has been achieved, in the points that a virtual image is suppressed and the resolving power is enhanced, and the noise level is still the same as a conventional level.

As described above, the ultrasonic imaging device according to the first embodiment establishes annular areas the number of which is larger than the number of signal lines M, the annular areas using as borders, line intersections between the two-dimensional surface of the probe 1 and multiple concentric spheres having the focal point as a center. Then, the ultrasonic imaging device selects out of the established annular areas, annular areas whose distance from the focal point are shifted by the ultrasonic wavelength $\lambda$, and connects the transducer elements of the selected annular areas to one signal line. Accordingly, it is possible to establish the annular areas the number of which is larger than the number of signal lines, narrowing the width of the annular area, and reduces the possibility that the signals from the transducer elements of an identical annular area cancel one another out. In the embodiment as described above, according to formula 1, the annular areas are established in such a manner that the distance from the focal point 410 varies by a constant value ($\lambda/N_1$), but the present invention is not limited to this configuration method. It is further possible that the annular areas are established in such a manner that the distance from the focal point 410 varies by a value which is not constant. In addition, it is further possible that the annular areas may be established in such a manner that the width of each of the annular areas is made constant on the two-dimensional surface of the probe 1. Further in such cases above, the annular areas are established under the condition that the number of annular areas exceeds the number of signal lines, the annular areas are selected which are positioned, each at a distance from the focal point being shifted by λ, and these selected annular areas are connected to one signal line, whereby it is possible to reduce the number of channels while the signals in the annular areas do not cancel one another out, and a certain effect can be obtained.

The ultrasonic diagnostic device according to the first embodiment is capable of improving the focused sound pressure by 100% to 300%, and therefore, it is suitable for an imaging method which gives a higher priority to the sound pressure, rather than the resolving power in the sound axis direction, for instance, Doppler imaging.

Second Embodiment

Next, an ultrasonic imaging device according to a second embodiment of the present invention will be explained. In the ultrasonic imaging device according to the second embodiment, in a similar manner as the first embodiment, annular areas are established, the number of which is larger than the number of signal lines. However, unlike the first embodiment, as shown in FIG. 16, the widths of the annular areas 421 to 42$p$ are not equivalent when converted into the ultrasonic wavelength, and nonuse annular areas 161 to 171 are provided, the transducer elements of which are not used for transmitting and receiving waves. In other words, as shown in FIG. 16, the areas indicated in white and black form one group of annular areas each having the different width when converted into ultrasonic wavelength, whereas the annular areas 161 to 171 being shaded, are areas having different widths when converted into ultrasonic wavelength, and these areas are not used for transmitting and receiving waves. The other configuration is the same as the first embodiment, and therefore, tedious explanations will not be made.

As a method for setting the nonuse areas 161 to 171 as shown in FIG. 16, for instance, there is one method that after the annular areas are established in a similar manner as the first embodiment, annular areas in a predetermined width from the innermost side or the outermost side thereof are set as the nonuse areas, and the selection part 2 does not connect the transducer elements in the nonuse areas with any of the signal lines. In the example of FIG. 16, multiple annular areas each having a width equal to or less than half wavelength, when converted in the ultrasonic wavelength, are established, and then, remaining areas are distributed between the established annular areas to set the nonuse area. However, they are not necessarily distributed between the annular areas.

As another method for setting the nonuse areas 161 to 171, for instance, it is possible to employ a method in which $N_1$ is set to be double the value of the first embodiment in the formula 1 according to the first embodiment, thereby setting annular areas the number of which is doubled, and in the formula 2, only the areas having $n_1$ that is odd-numbered or even-numbered are selected. With the method above, either the areas having $n_1$ that is odd-numbered or the areas having $n_1$ that is even-numbered can be set as the nonuse annular areas 161 to 171.

In the second embodiment, the maximum distance of the transducer elements to be connected to the same signal line can be narrowed more, relative to the first embodiment, and therefore, a high resolving power can be obtained in the sound axis direction. Simultaneously, the width of the annular area is equal to or less than half-wavelength when converted into ultrasonic wavelength, and the signals outputted from the transducer elements within the same annular area do not cancel one another out by the addition via the signal lines, and the pulses being canceled out are removed, when delay addition is performed, thereby reserving a certain focused sound pressure. In the second embodiment, it is possible to improve the focused sound pressure at the most within the range not damaging the resolving power in the sound axis direction. Therefore, this method is suitable for the imaging in the case where the resolving power in the sound axis direction is given a priority to the focused sound pressure, such as an RF imaging and imaging of fine structure.

Third Embodiment

Next, an explanation will be made regarding an ultrasonic imaging device according to a third embodiment of the present invention. The ultrasonic imaging device according to the third embodiment establishes areas the number of which is larger than the number of signal lines, in a similar manner as the first embodiment. However, unlike the first embodiment, a shape of the areas is not limited to the annular shape. In addition, a mean value or a central value of the distances between the transducer elements belonging to the area and the focal point is calculated, and this is assumed as a distance between the focal point and the areas. Since the other configuration is the same as the first embodiment, a tedious explanation will not be made.

In the third embodiment, the shape of the area is not limited to the annular, the present invention can be applied to an area that is not annular in shape which is configured on the basis of electric consistency, for example, impedance matching, or it can be applied to a sparse array area configured on the basis of grating suppression by introducing randomness. Therefore, it is possible to achieve both effects; electric consistency or grating suppression by introducing randomness, and attainment of a focused sound pressure.

DENOTATION OF REFERENCE NUMERALS

Figure 1:
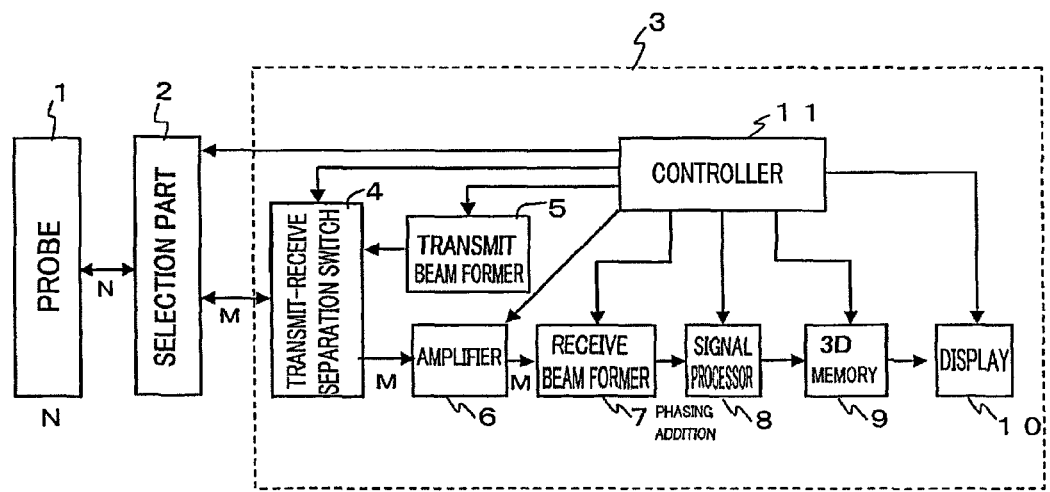
FIG. 1 is a block diagram showing an device configuration of the ultrasonic imaging device according to an embodiment of the present invention.
Figure 2:
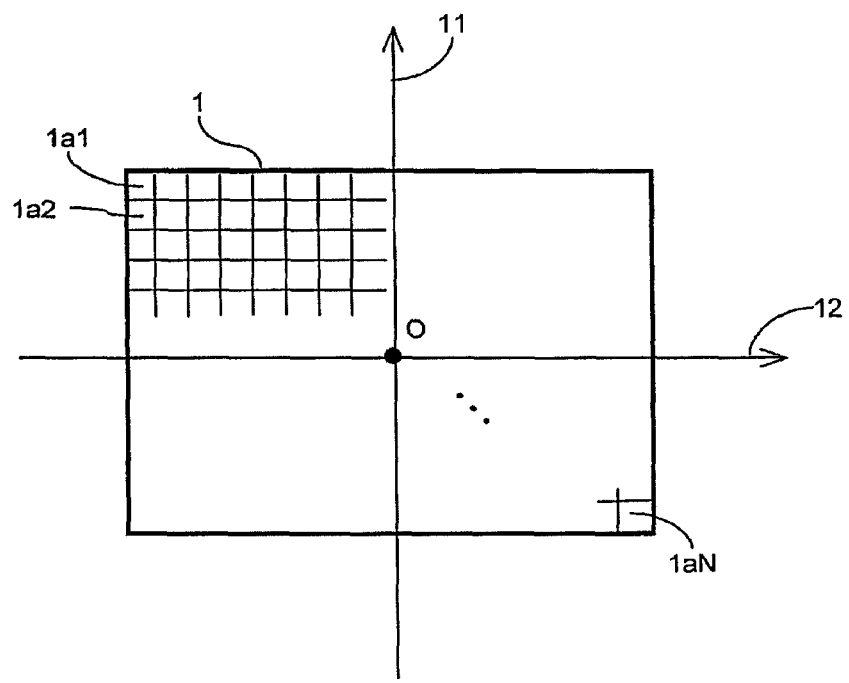
FIG. 2 illustrates the arrangement of the transducer elements in the probe 1 of the ultrasonic imaging device according to the embodiment.
Figure 3:
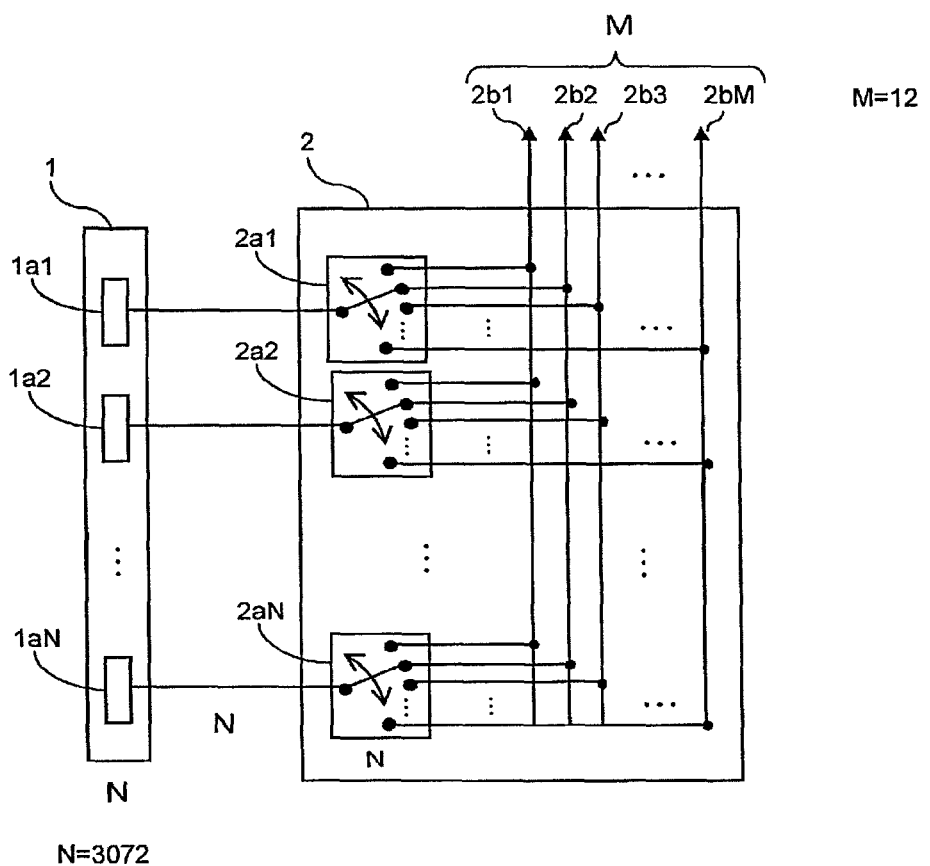
FIG. 3 is a block diagram showing a configuration of the probe 1 and the selection part 2 of the ultrasonic imaging device according to the embodiment.
Figure 4:
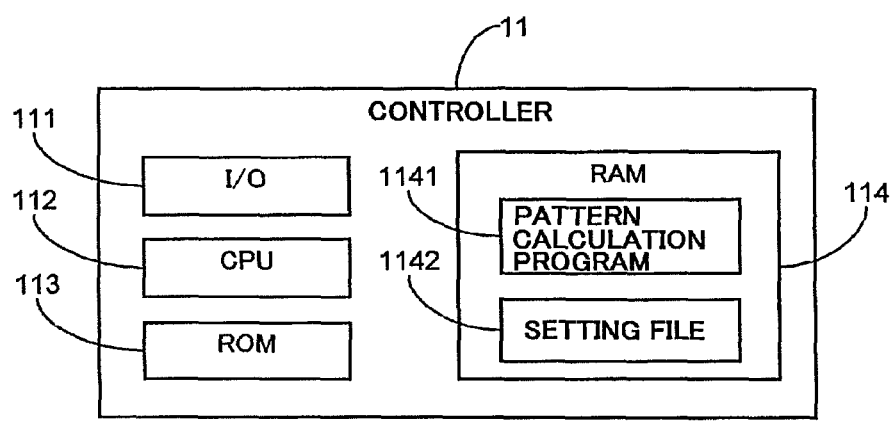
FIG. 4 is a block diagram showing a configuration of the controller 11 of the ultrasonic imaging device according to the embodiment.
Figure 5:
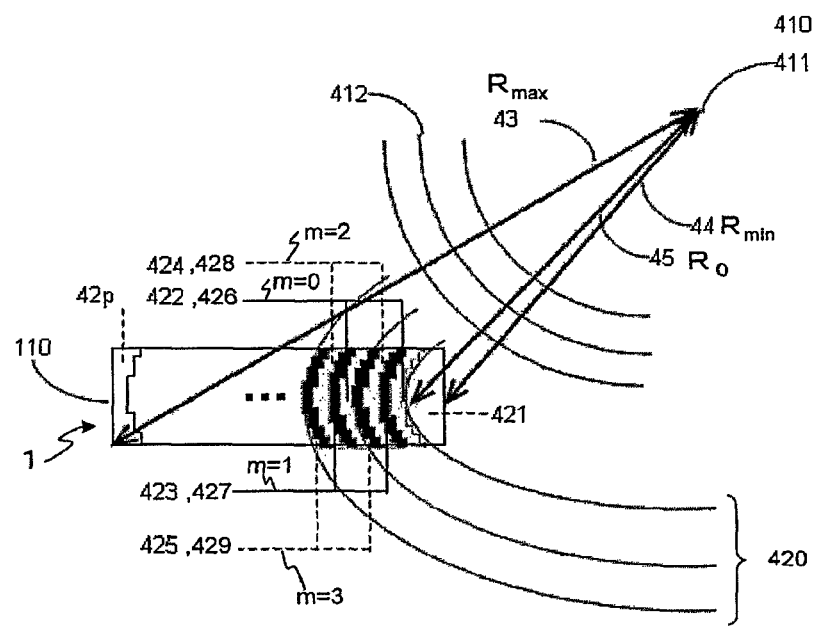
FIG. 5 illustrates the annular areas established by the controller 11 shown in FIG. 4.
Figure 6A:
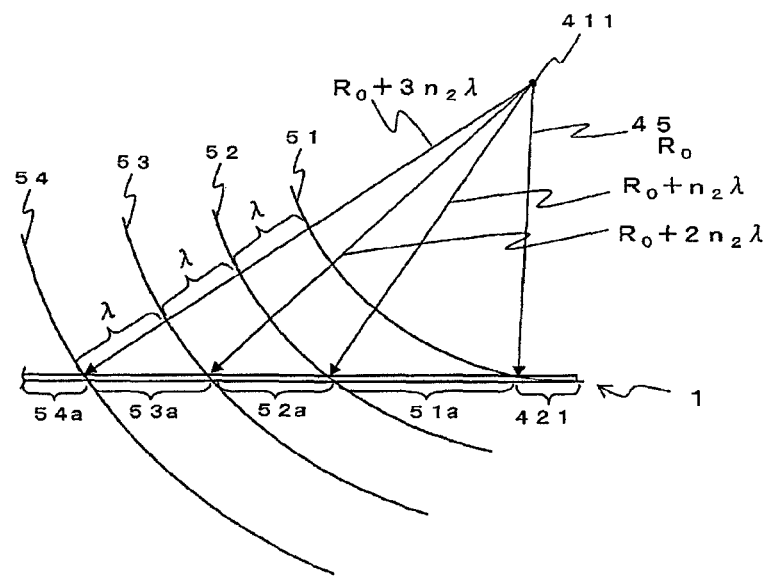
FIG. 6($a$) and FIG. 6($b$) illustrate a concept how the controller as shown in FIG. 4 establishes the annular areas.
Figure 6B:
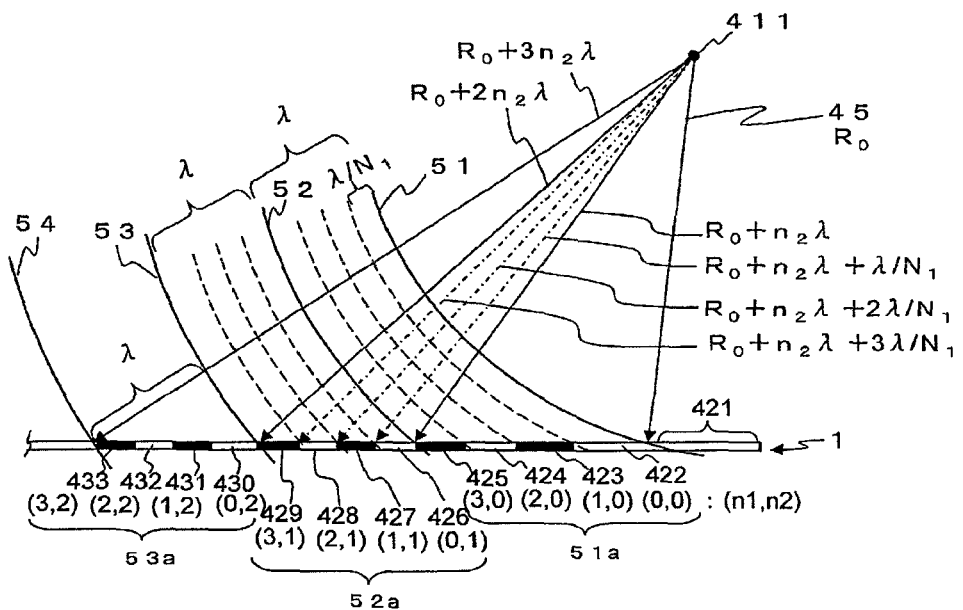
Figure 7:
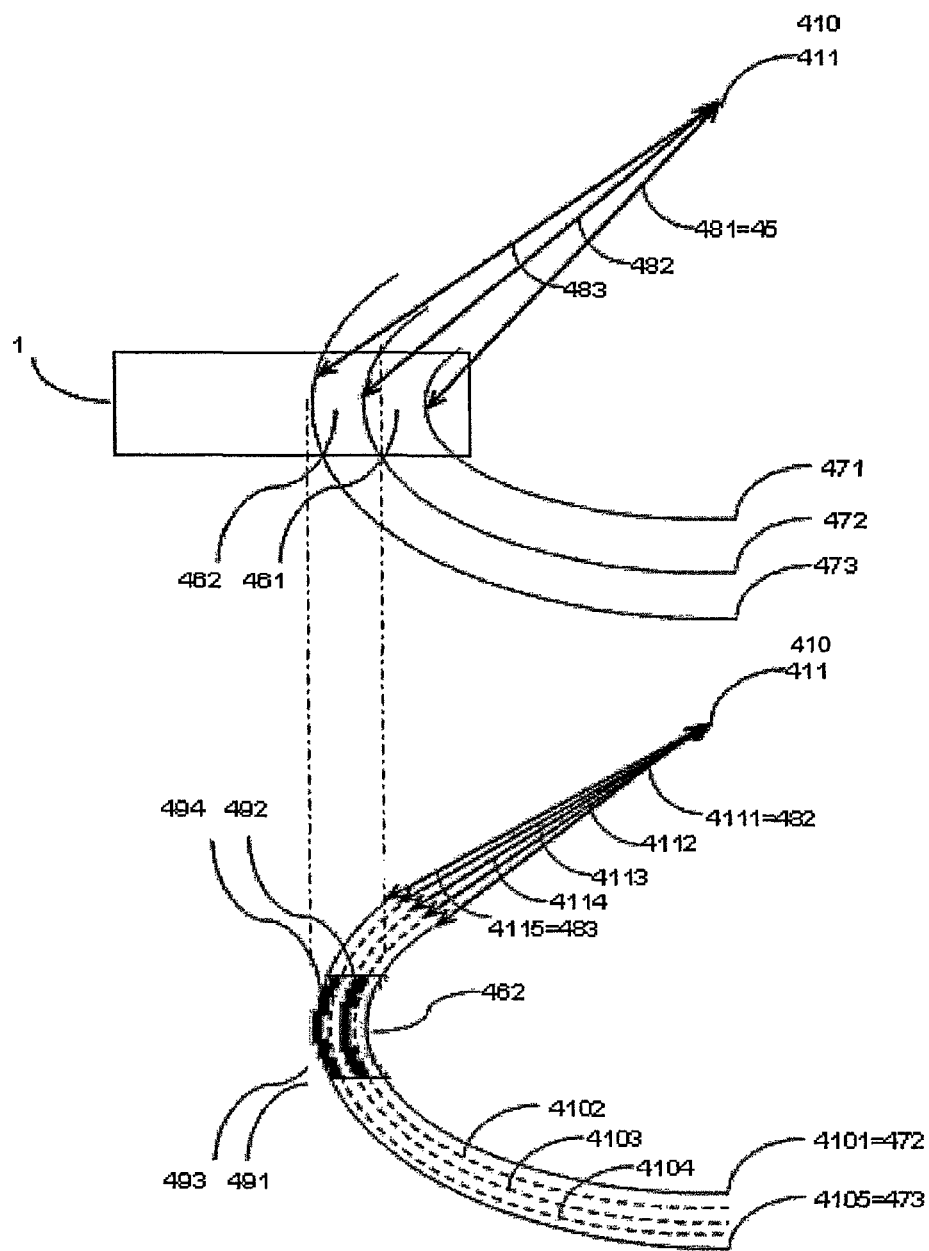
FIG. 7 illustrates the annular areas established by the controller 11 as shown in FIG. 4.
Figure 8:
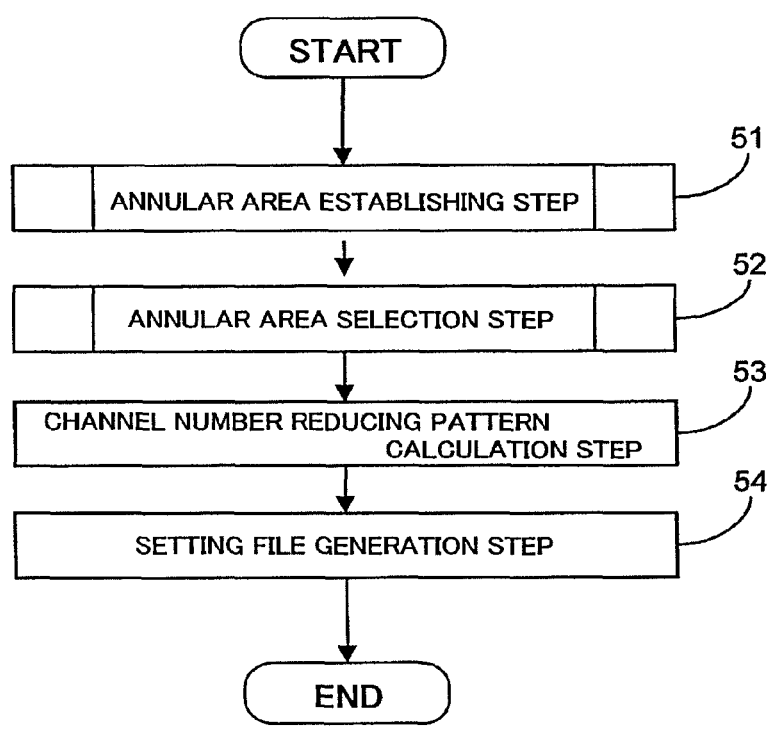
FIG. 8 is a flowchart showing an operation of the controller 11 as shown in FIG. 4.
Figure 9:
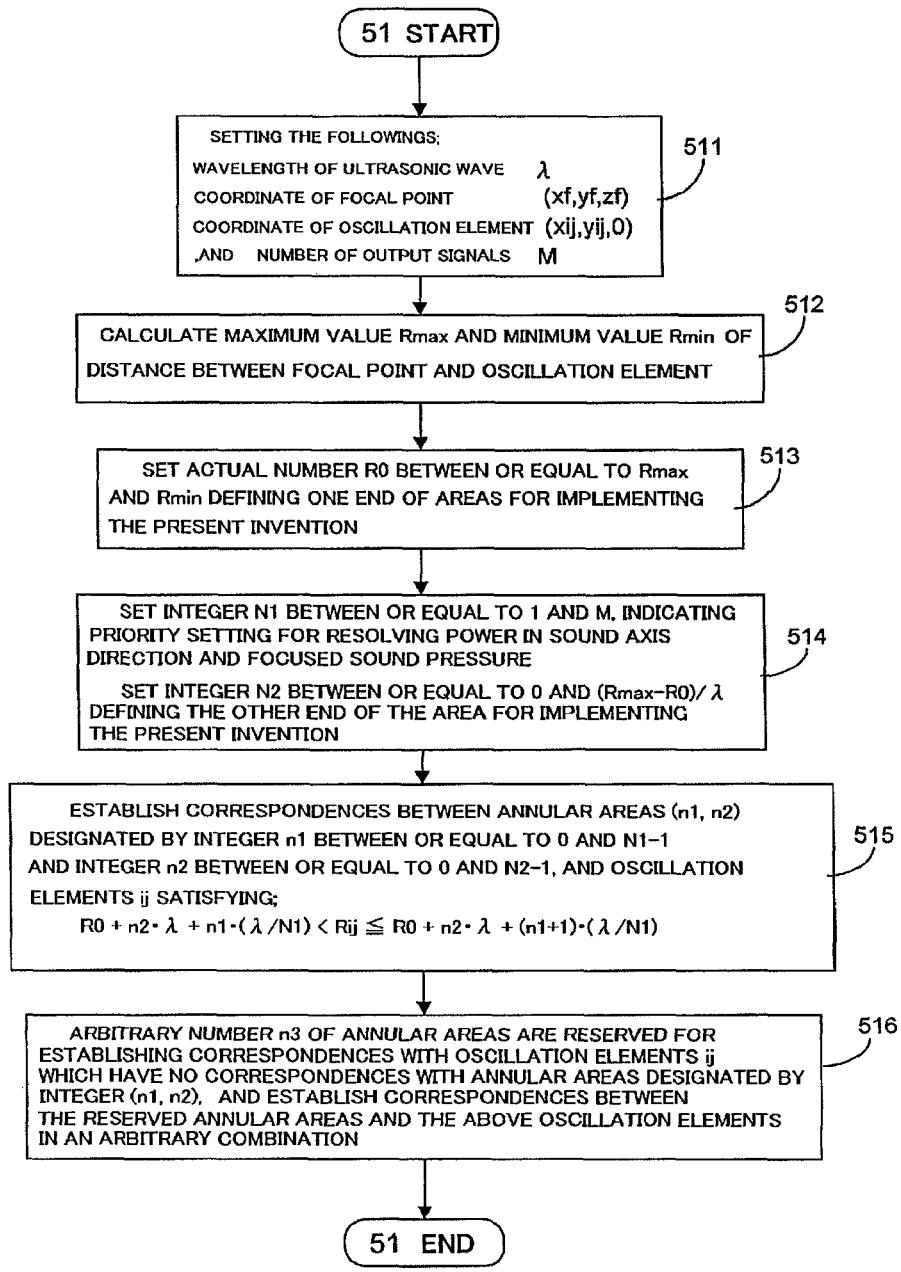
FIG. 9 is a flowchart showing details of the step 51 in FIG. 8.
Figure 10:
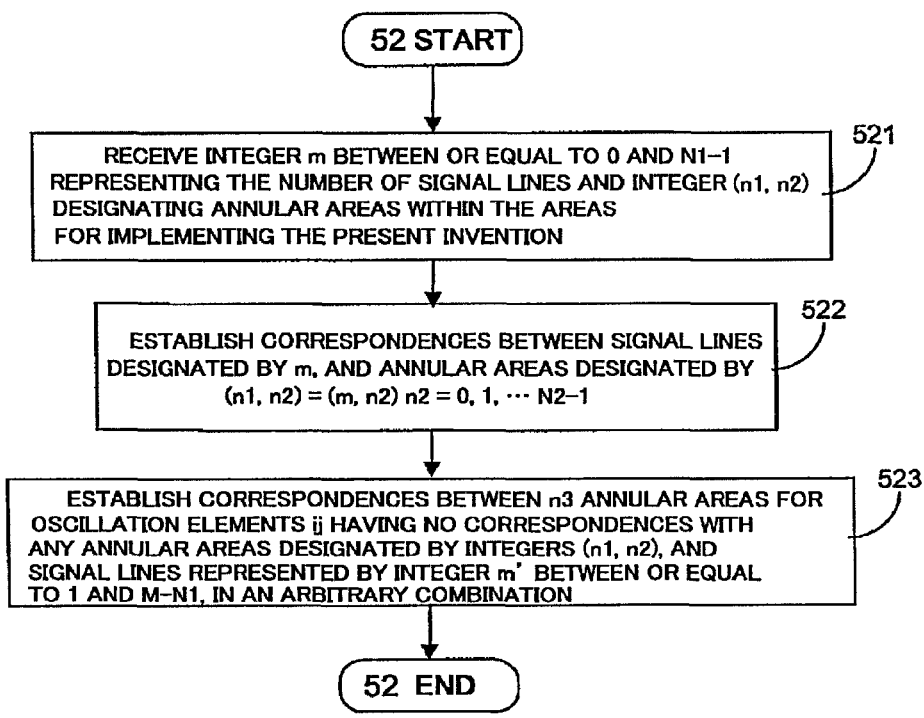
FIG. 10 is a flowchart showing details of the step 52 in FIG. 8.
Figure 11A:
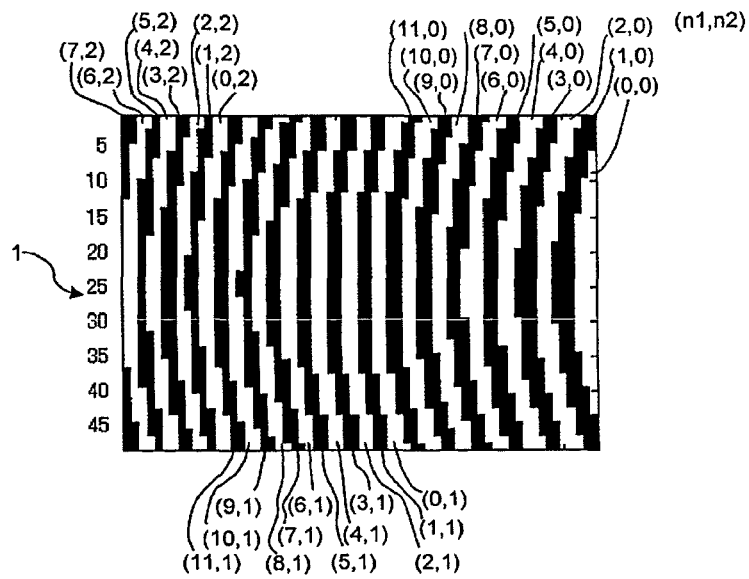
FIG. 11(a) illustrates a part of the annular areas being established according to the first embodiment.
Figure 11B:
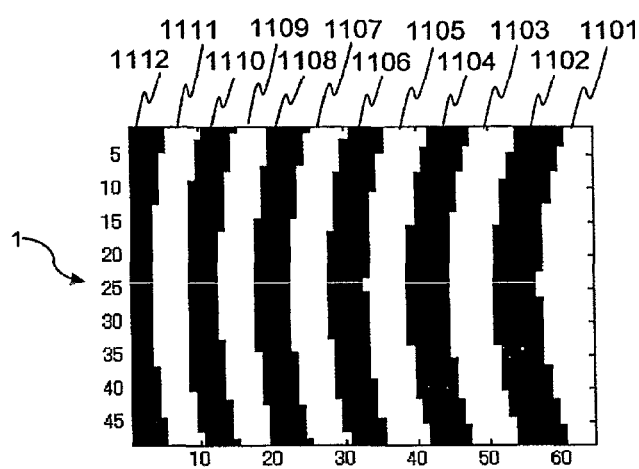
FIG. 11(b) illustrates the annular areas the number of which is the same as the number of channels, as a comparative example.
Figure 12A:
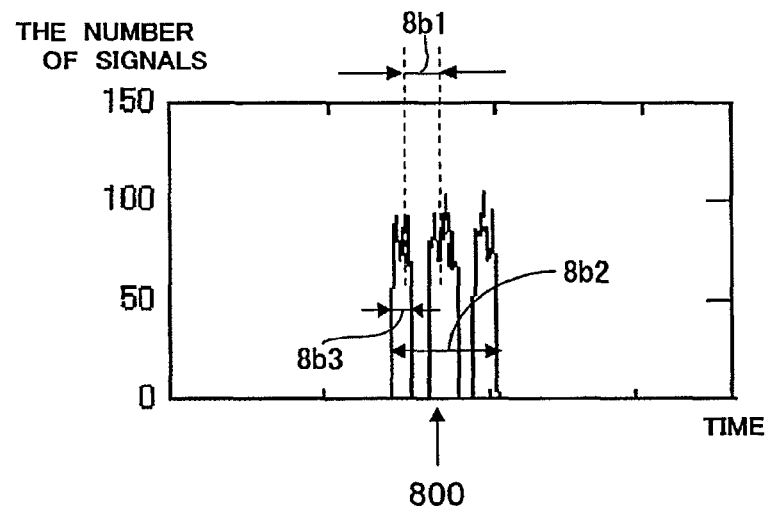
FIG. 12(a) is a graph showing a signal waveform after delaying and summing operations by the receive beam former 7 according to the first embodiment.
Figure 12B:
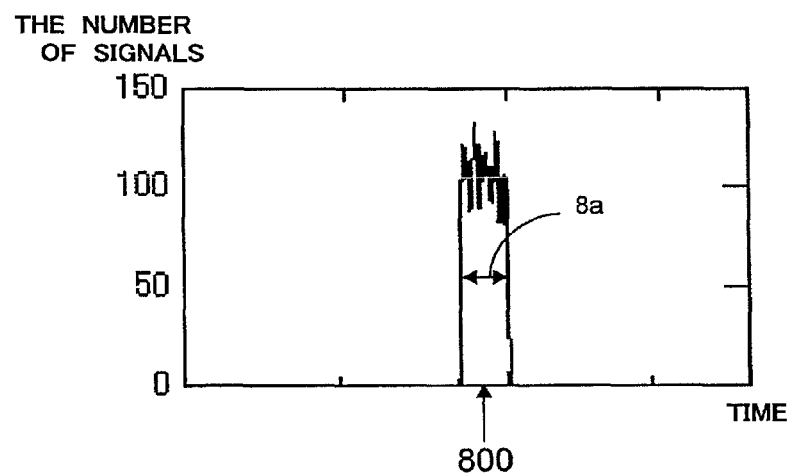
FIG. 12(b) is a graph showing a signal waveform after delaying and summing the signals from the annular areas as shown in FIG. 11(b) being the comparative example.
Figure 13A:
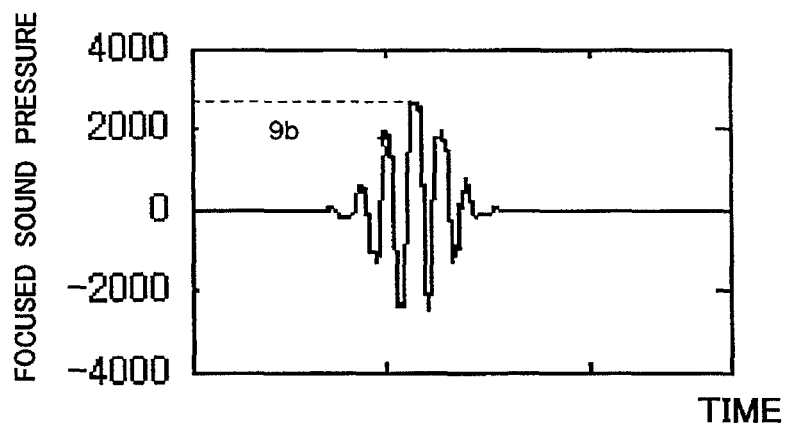
FIG. 13(a) is a graph showing a temporal waveform of the focused sound pressure of the signals obtained by the receive beam former 7.
Figure 13B:
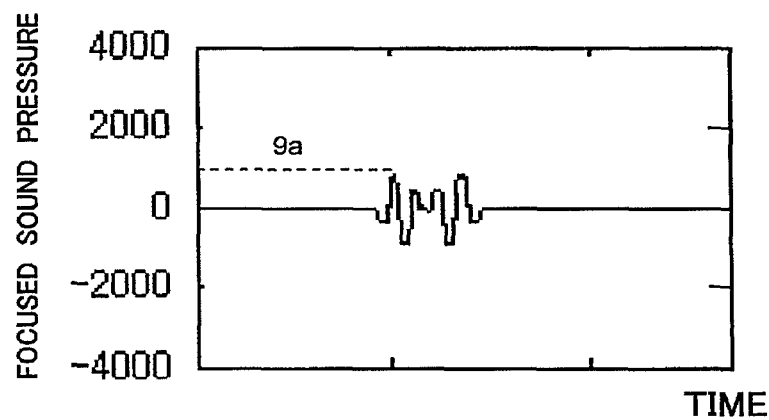
FIG. 13(b) is a graph showing a temporal waveform of the focused sound pressure of the signals obtained by the comparative example.
Figure 14:
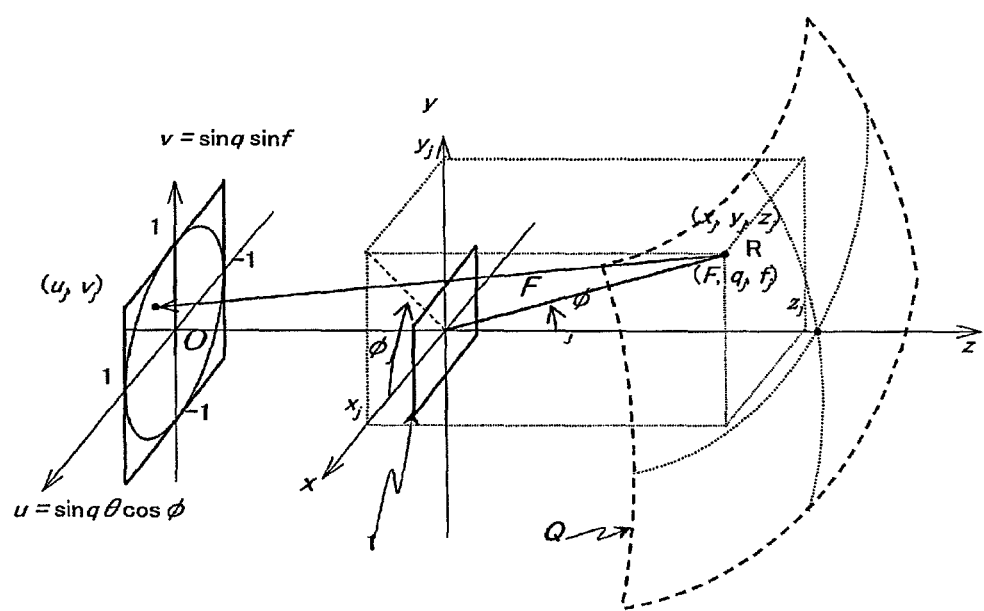
FIG. 14 illustrates a display coordinate system when values obtained by integrating the temporal waveform of the focused sound pressure with respect to each angle on the hemispherical face, are subjected to the point spread function.
Figure 15A:
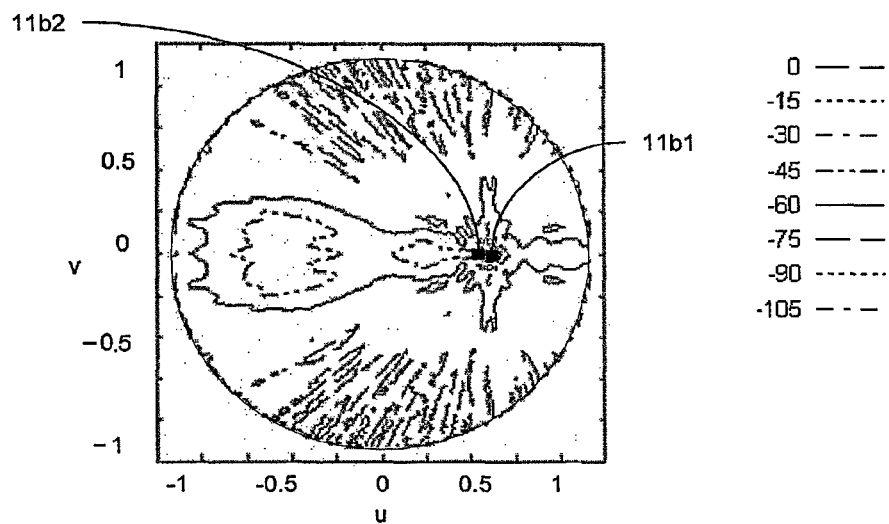
FIG. 15(a) shows a contour plot of the point spread function obtained from the temporal waveform of the focused sound pressure of the received signals according to the first embodiment.
Figure 15B:
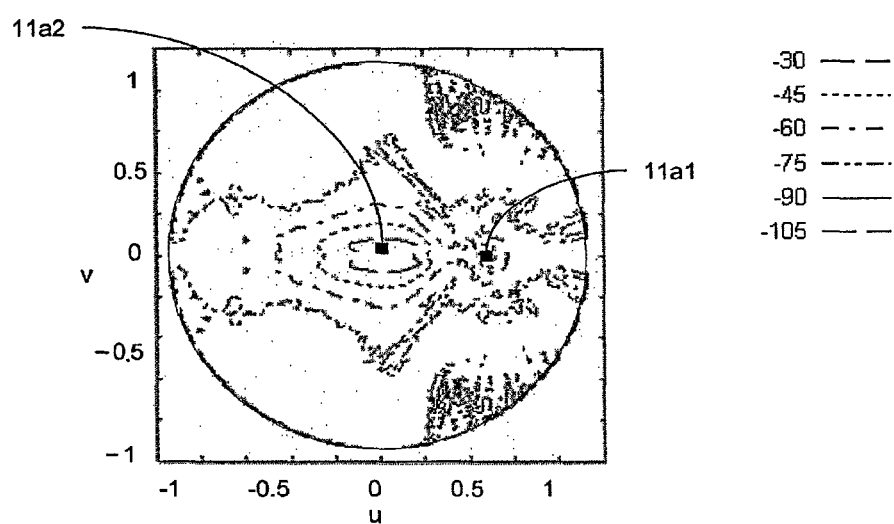
FIG. 15(b) shows a contour plot of the point spread function obtained from the temporal waveform of the focused sound pressure of the received signals according to the comparative example.
Figure 16:
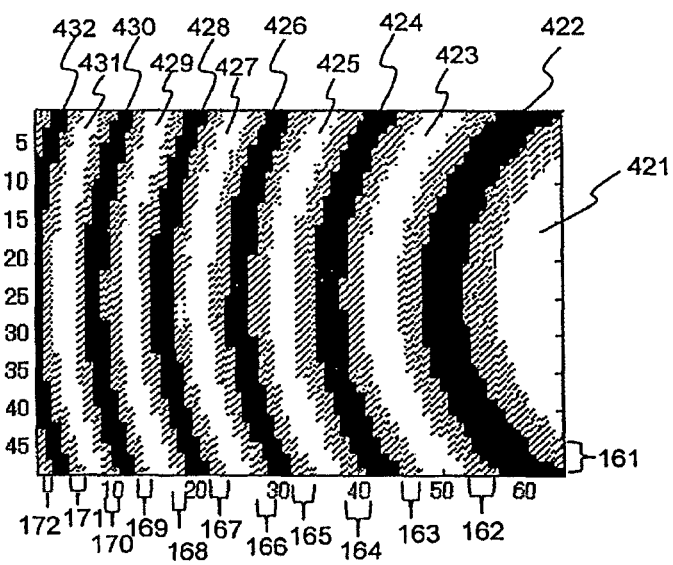
FIG. 16 illustrates the annular areas established by the controller of the ultrasonic imaging device according to the second embodiment.

1: PROBE, 2: SELECTION PART, 3: DEVICE MAIN UNIT, 4: TRANSMIT-RECEIVE SEPARATION SWITCH, 5: TRANSMIT BEAM FORMER, 6: AMPLIFIER, 7: RECEIVE BEAM FORMER, 8: SIGNAL PROCESSOR, 9: THREE-DIMENSIONAL MEMORY, 10: DISPLAY PART, 11: CONTROLLER, 51 TO 54: WAVE SURFACES, 410: FOCAL POINT, 411: VIRTUAL POINT SOUND SOURCE, 412: WAVE SURFACE, 420: LINE INTERSECTION BETWEEN ULTRASONIC WAVE SURFACES AND PROBE SURFACE, 421 TO 42p: ANNULAR AREAS, 430: WIDTH OF ANNULAR AREA

What is claimed is:

1. An ultrasonic imaging device comprising,
multiple transducer elements which are arranged in a multi-dimensional array in a first direction and in a second direction,
a probe having the multiple transducer elements, for transmitting an ultrasonic wave of wavelength $\lambda$ to a predetermined focal point of an object and receiving a reflected wave,
M signal lines, the number of which is less than a number of the multiple transducer elements,
a selection part for connecting selected transducer elements, with any of the multiple transducer elements, with any of signal lines selected out of the multiple signal lines,
a controller for controlling an operation of the selection part, and
a beamformer for delaying signals outputted from the multiple signal lines by a predetermined amount with respect to each of the signal lines, and summing the signals, wherein,
when it is assumed that a maximum value of a distance between the focal point and the multiple transducer elements is Rmax, a minimum value of the distance between the focal point and the multiple transducer elements is Rmin, a distance between the focal point and the multiple transducer elements at i-th position and j-th position respectively in the first direction and the second direction is Rij, a predetermined actual number between or equal to Rmin and Rmax is R0, a predetermined integer between or equal to 1 and M is N1, an arbitrary integer between or equal to 0 and N1−1 is n1 (n1=0, 1, . . . N1−1), a predetermined integer between or equal to 0 and (Rmax−R0)/λ is N2, and an arbitrary integer between or equal to 0 and N2−1 is n2 (n2=0, 1, . . . N2−1), the controller establishes an annular area for each combination of n1 and n2, the annular area being made up of multiple transducer elements having Rij which satisfies the formula 1 as the following, wherein the controller treats the multiple transducer elements as arranged in multiple concentric spheres respectively having differing radii about the focal point, and establishes areas sectioned by the line intersections between the multiple concentric spheres and the multi-dimensional surface, as annular areas, where the number of annular areas is larger than the number of signal lines:

$$R0+n2\cdot\lambda+n1\cdot(\lambda/N1)<Rij\leq R0+n2\cdot\lambda+(n1+1)\cdot(\lambda/N1) \quad \text{(formula I)},$$

and
the controller selects predetermined multiple annular areas having differing radii out of the multiple annular areas being established, and controls the selection part to connect the multiple transducer elements constituting the predetermined multiple annular areas being selected, as the selected transducer elements, with an identical signal line.

2. The ultrasonic imaging device according to claim 1
the multiple transducer elements as arranged in the multiple concentric spheres respectively having the radii differing by a predetermined constant value about the focal point.

3. The ultrasonic imaging device according to claim 2, wherein,
the number of the signal lines is M, and when a predetermined integer between or equal to 1 and M is assumed as N1 and the ultrasonic wavelength is assumed as $\lambda$, the radii of the multiple concentric spheres are different by $\lambda/N1$.

4. The ultrasonic imaging device according to claim 1, wherein, the controller treats, wherein,
the controller selects annular areas not adjacent to each other.

5. The ultrasonic imaging device according to claim 1, wherein,
the controller establishes a nonuse annular area between adjacent annular areas, where ones of the multiple transducer elements within the nonuse annular area are not used for an ultrasonic imaging, and controls the selection part not to connect the ones of the multiple transducer elements positioned within the nonuse annular area, with any of the signal lines.

6. The ultrasonic imaging device according to claim 1, wherein, the controller changes a position and a selection of the annular areas, in order to change the focal point.

7. The ultrasonic imaging device according to claim 6, wherein,
the controller has a storage and performs an arithmetical operation in advance to establish and select the annular areas, with respect to each position that is settable as the focal point, and stores a result of the operation in the storage, and the controller reads the operation result stored in the storage, according to the focal position at that point of time, and controls the selection part according to the read operation result.

8. The ultrasonic imaging device according to claim 1, wherein,
the controller selects multiple annular areas with focal depths differing by an integral multiple of the ultrasonic wavelength, out of the multiple annular areas being established.

9. The ultrasonic imaging device according to claim 1, wherein,
when the annular areas established as a combination of n1 and n2 according to the formula 1, are represented as (n1, n2), the controller selects N2 annular areas represented by (m, 0), (m, 1), (m, 2) . . . (m, N2−1) for the m-th signal line, and connects the multiple transducer elements in these annular areas with the m-th signal line.

* * * * *